United States Patent
Stensrud et al.

(10) Patent No.: US 9,630,974 B2
(45) Date of Patent: Apr. 25, 2017

(54) PROCESS FOR ACID DEHYDRATION OF SUGAR ALCOHOLS

(71) Applicant: ARCHER DANIELS MIDLAND COMPANY, Decatur, IL (US)

(72) Inventors: Kenneth Stensrud, Decatur, IL (US); Erik Hagberg, Decatur, IL (US); Stephen Howard, Sherman, IL (US); Erin M Rockafellow, Decatur, IL (US)

(73) Assignee: Archer-Daniels-Midland Co.

( * ) Notice: Subject to any disclaimer, the term of this patent is extended or adjusted under 35 U.S.C. 154(b) by 0 days.

(21) Appl. No.: 14/771,825

(22) PCT Filed: Feb. 21, 2014

(86) PCT No.: PCT/US2014/017563
§ 371 (c)(1),
(2) Date: Sep. 1, 2015

(87) PCT Pub. No.: WO2014/137619
PCT Pub. Date: Sep. 12, 2014

(65) Prior Publication Data
US 2016/0016970 A1    Jan. 21, 2016

Related U.S. Application Data

(60) Provisional application No. 61/772,642, filed on Mar. 5, 2013.

(51) Int. Cl.
*C07D 493/00* (2006.01)
*C07D 493/04* (2006.01)

(52) U.S. Cl.
CPC .................. *C07D 493/04* (2013.01)

(58) Field of Classification Search
None
See application file for complete search history.

(56) References Cited

U.S. PATENT DOCUMENTS 3,223,734 A * 12/1965 Fallstad .................. A61K 8/41
203/DIG. 6

FOREIGN PATENT DOCUMENTS

WO    WO 2012/081785 A1 *  6/2012

OTHER PUBLICATIONS

Rebacz, NA. et al. Hydration and Hydrolysis with Water Tolerant Lewis Acid Catalysts in High Temperature Water. University of Michigan. 2011, p. 57.*
Loudon, M. et al. Organic Chemistry 5th Edition. WH Freeman. 2009, p. 436-437.*
Liu, F. et al. Catalytic etherification of glycerol with short chain alkyl alcohols in the presence of Lewis acids. Green Chemistry. 2013, vol. 15, p. 908.*

* cited by examiner

*Primary Examiner* — Noble Jarrell
*Assistant Examiner* — Ben S Michelson
(74) *Attorney, Agent, or Firm* — William B. Miller

(57) ABSTRACT

A process is described for the acid-catalyzed dehydration of a sugar alcohol, wherein the catalyst comprises a water-tolerant Lewis acid. In particular embodiments, the catalyst comprises a homogeneous water-tolerant Lewis acid, especially a homogeneous Lewis acid selected from the group consisting of bismuth (III) triflate, gallium (III) triflate, scandium (III) triflate, aluminum triflate, tin (II) triflate and indium (III) triflate. Such catalysts are effective for dehydrating both of sorbitol and the 1,4-sorbitan dehydration precursor of isosorbide, and bismuth (III) triflate particularly is beneficial for dehydrating mannitol to isomannide.

3 Claims, No Drawings

PROCESS FOR ACID DEHYDRATION OF SUGAR ALCOHOLS

BACKGROUND OF THE INVENTION

The present invention is concerned with processes for making dehydration products from sugar alcohols, and more particularly but without limitation, to acid-catalyzed processes for making isohexides, such as isosorbide, from hexitols such as sorbitol or from monoanhydrohexitols such as 1,4-sorbitan.

The dehydration products that can be made by the acid-catalyzed double dehydration of sugar alcohols (that is, by removing two waters in succession from a sugar alcohol), in particular, hexitols such as sorbitol, have been the subject of extensive work. Isosorbide, also known as 1,4,3,6-dianhydrosorbitol, is now commercially produced and marketed as a monomer for imparting renewable content to polyesters and polycarbonates, and has been used as a pharmaceutical intermediate.

A variety of acid catalysts have been evaluated for use in carrying out the dehydration of sorbitol through certain monoanhydrohexitol intermediates (e.g., 1,4-sorbitan) isosorbide. Inorganic acids such as $H_2SO_4$, $H_3PO_4$, and HCI are readily obtained, inexpensive materials but are difficult to regenerate. In order to avoid the regeneration and attendant disposal problems, solid resin catalysts have been tried. Unfortunately, in the presence of water and at the temperatures required for carrying out the dehydration, very few solid acids can demonstrate the activity and stability needed to begin to contemplate a commercially viable process.

U.S. Pat. Nos. 6,849,748; 7,420,067; 7,439,352; 7,772,412 and 7,982,059 provide examples of prior art methods for producing isohexides (also referred to as anhydrosugar alcohols, anhydrohexitols, anhydroalditols etc) such as isosorbide, from sorbitol from dextrose.

Commonly-assigned U.S. Pat. No. 6,849,748 to Moore at al., for example, describes a solvent-free process wherein a sugar alcohol—such as sorbitol—is heated with stirring until molten, and then dehydrated in the presence of a soluble acid or acidic on exchange resin with stirring, under vacuum (to remove the water product and drive the reaction toward the products) and at an elevated temperature, then the resulting anhydrosugar alcohol is purified by distillation, followed by melt crystallization and/or redistillation. The final, purified product is isolated by centrifugation or filtration. Enumerated preferred acid catalysts include sulfuric acid, phosphoric acid, p-toluenesulfonic acid and p-methanesulfonic acid.

Commonly-assigned U.S. Pat. No. 7,420,067 mentions these same acids, as well as acidic ion exchange resins and acidic zeolite powders as additional options. Successive film evaporators, especially wiped film evaporators under vacuum, are described for use in purifying the product isosorbide.

U.S. Pat. No. 7,772,412 to Holladay et al. describes a process for making isosorbide wherein sorbitol is fed to as reactor containing a dehydration catalyst and a hydrogenation co-catalyst, with hydrogen being supplied countercurrently to the reactor for removing water as it is formed and for "reducing or eliminating . . . oligomeric or polymeric material in the dehydrator product", to which undesirable color formation had been attributed. Suitable dehydration catalysts include the mineral acid catalysts, solid acid catalysts such as the heteropolyacids, mesoporous silicas, acid clays, sulfated zirconia, molecular sieve materials, cation exchange resins and zeolites, and combinations of any of these. The hydrogenation catalyst is described as typically being a supported metal or multi-metal catalyst. Palladium in particular is described as especially preferable for the metal, with platinum, nickel, cobalt, ruthenium, rhenium, rhodium, iridium and iron also being listed.

U.S. Pat. No. 7,982,059 describes a process for converting aqueous sorbitol to xylitol and isosorbide in the presence of an acid catalyst and without a hydrogenation co-catalyst, more particularly involving reacting an aqueous sorbitol solution with an acid zeolite at about 250 degrees Celsius and a pressure maintained at from about 68 bars to about 80 bars to produce the xylitol and isosorbide.

WO 2013/138153 to Binder et al. describes a process for forming one or more dehydration products from an aqueous sugar alcohols solution including one or more alcohols from pentoses and hexoses, wherein the aqueous sugar alcohols solution is subjected to an acid-catalyzed dehydration using a substituted sulfonic acid catalyst solubilized in the aqueous sugar alcohols solution. In certain preferred embodiments, the dehydration process is conducted rapidly and with rapid cooling of the dehydration products prior to any separation of the residual sugar alcohol(s) from the dehydration products in the overall product mixture, in the manner prescribed for the dehydration of aqueous sugar solutions in WO 2013/106136 to Sanborn et al.

SUMMARY OF THE INVENTION

The following presents a simplified summary of the invention in order to provide a basic understanding of some of its aspects. This summary is not an extensive overview of the invention and is intended neither to identify key or critical elements of the invention nor to delineate its scope. The sole purpose of this summary is to present some concepts of the invention in a simplified form as a prelude to the more detailed description that is presented later.

With this in mind, the present invention in a first aspect concerns a process for the acid-catalyzed dehydration of a sugar alcohol, wherein the catalyst comprises a water-tolerant Lewis acid. In particular embodiments, the catalyst comprises a homogeneous water-tolerant Lewis acid, especially a homogeneous Lewis acid selected from the group consisting of bismuth (III) triflate, gallium (III) triflate, scandium (III) triflate, aluminum triflate, tin (III) triflate and indium (III) triflate. Such catalysts are effective for dehydrating both of sorbitol and the 1,4-sorbitan dehydration precursor of isosorbide, and bismuth (III) triflate particularly is beneficial for dehydrating mannitol to isomannide, so that in a second, more particular aspect the present invention concerns an improved process for making an isohexide from a corresponding hexitol.

DETAILED DESCRIPTION OF PREFERRED EMBODIMENTS

A preferred process according to the present invention for dehydrating sorbitol involves mixing sorbitol with from 0.005 mol percent and greater of a water-tolerant Lewis acid, heating to at least 140 degrees Celsius, and carrying out the acid-catalyzed dehydration of sorbitol isothermally for an hour or longer under a reduced pressure to continuously remove water from the reaction. The water-tolerant Lewis acid is preferably one or more of bismuth (III) triflate, gallium (III) triflate, scandium (III) triflate, aluminum triflate, tin (II) triflate and indium (III) triflate, and while yields of isosorbide and the 1,4-sorbitan precursor of isosorbide obtained from these catalysts can be seen from the examples below to vary somewhat dependent on the catalyst used, the catalyst loading and reaction conditions of temperature and duration, it is expected that catalyst loadings of not more than 0.1 mol percent, temperatures of not more than 160 degrees Celsius and reaction times of not more than 3 hours will provide commercially acceptable yields of isosorbide. The crude product mixture may then be purified according to any of the known methods for doing so.

As will be evident from the examples that follow, use of the preferred Lewis acids under these conditions provides a number of benefits, including enhanced yields of isosorbide and of the 1,4-sorbitan precursor of isosorbide as compared to the most effective Brönsted acid surveyed, namely, sulfuric acid, much reduced catalyst loadings for achieving a targeted yield of isosorbide, avoidance of the neutralization requirements posed by the conventional Brönsted acids before distillation of the crude product mixture and better color of the crystalline isosorbide distillates that may be realized.

While some or all of these benefits are expected to be attainable in the dehydration of sugar alcohols generally (where "sugar alcohols" is understood to include partially dehydrated sugar alcohols such as, for example, monoanhydrohexitols from the partial dehydration of hexitols), the extent to which certain benefits or advantages are observed, the particular water-tolerant Lewis acid catalysts that prove most effective and the optimum process conditions for carrying out the Lewis acid-catalyzed dehydrations can be expected to vary somewhat from one sugar alcohol to the next. As an example, we found bismuth triflate to be particularly advantageous for catalyzing the dehydration of mannitol to isomannide. Those skilled in the art will be well able, in any event, to determine the optimum features of a process for dehydrating a particular sugar alcohol using a water-tolerant, Lewis acid catalyst as claimed herein by routine experimentation.

The present invention is further illustrated by the following, non-limiting examples:

COMPARATIVE EXAMPLES 1-6

For benchmarking the performance of the water-tolerant Lewis acid catalysts of the present invention, a number of Brönsted acids were evaluated for the acid-catalyzed dehydration of sorbitol. In each instance, a three neck, 250 mL round bottomed flask equipped with a magnetic stir bar was charged with 100 grams of sorbitol (0.549 mol), then was immersed in an oil bath set at 140 degrees Celsius. Once the sorbitol liquefied and attained an internal temperature of 140 degrees as determined by an internal temperature probe, a quantity (2 mol percent in all cases except for phosphoric acid, which was added at 5 mol percent) of the Brönsted acid in question was introduced by syringe through a rubber septum-capped neck. Under a reduced pressure of less than 5 torr, the reaction was then continued isothermally for 1 hour. After this time, the vacuum was broken, the crude product mixture was cooled and quenched with 50 percent aqueous sodium hydroxide, then was weighed and quantitatively analyzed by gas chromatography. The results, shown in Table 1, show that sulfuric acid was the most effective Brönsted acid of those surveyed for dehydrating sorbitol under the indicated conditions, though unidentified side products accounted for about 23 percent of the crude product mixture.

TABLE 1

| Acid | pKa | % sorbitol conversion | Isosorbide yield (mol %) | 1,4-sorbitan yield (mol %) | 2,5-sorbitan yield (mol %) | Accountability (wt %) |
|---|---|---|---|---|---|---|
| Sulfuric | −5 | 100.00 | 67.72 | 0.00 | 9.30 | 76.95 |
| p-toluenesulfonic | −2.8 | 100.00 | 22.83 | 54.90 | 9.30 | 87.00 |
| Methanesulfonic | −1.9 | 100.00 | 18.20 | 59.30 | 8.70 | 86.20 |
| Oxalic | 1.25 | 12.88 | 0.00 | 3.62 | 1.48 | 92.22 |
| Betaine HCl | 1.84 | 14.30 | 0.00 | 4.40 | 1.33 | 91.14 |
| Phosphoric | 2.14 | 72.00 | 5.18 | 55.98 | 3.15 | 92.31 |

COMPARATIVE EXAMPLE 7 AND EXAMPLES 1-6

The same experimental setup, procedure and conditions were used as in Comparative Examples 1-8, except that 0.1 mol percent of various Lewis acids (for Examples 1-6) or 0.1 mol percent of sulfuric acid (for Comparative Example 7) was used. The results were as shown in Table 2, follows:

TABLE 2

| Acid | % sorbitol conversion | Isosorbide yield (mol %) | 1,4-sorbitan yield (mol %) | 2,5-sorbitan yield (mol %) | Accountability (wt %) |
|---|---|---|---|---|---|
| Bi(OTf)$_3$ | 83.49 | 7.05 | 69.78 | 6.44 | 100.00 |
| In(OTf)$_3$ | 86.11 | 7.70 | 66.77 | 6.99 | 98.40 |
| Sc(OTf)$_3$ | 94.73 | 12.93 | 75.02 | 7.97 | 100.00 |
| Ga(OTf)$_3$ | 95.13 | 12.50 | 72.36 | 7.76 | 99.64 |
| Sn(OTf)$_3$ | 53.10 | 2.38 | 43.28 | 3.67 | 99.17 |
| Al(OTf)$_3$ | 80.04 | 5.76 | 65.51 | 5.84 | 98.73 |
| Sulfuric | 62.97 | 3.39 | 54.86 | 4.42 | 100.00 |

COMPARATIVE EXAMPLE 8 AND EXAMPLES 7-12

The same experimental setup, procedure and conditions were used as in Comparative Example 7 and Examples 1-6 (0.1 mol percent of catalyst), except that the reaction was continued for 2 hours at 140 degrees Celsius after introduction of the catalyst, as opposed to 1 hour. The results are shown in Table 3:

TABLE 3

| Acid | % sorbitol conversion | Isosorbide yield (mol %) | 1,4-sorbitan yield (mol %) | 2,5-sorbitan yield (mol %) | Accountability (wt %) |
|---|---|---|---|---|---|
| Bi(OTf)$_3$ | 99.53 | 23.73 | 61.06 | 7.67 | 94.98 |
| In(OTf)$_3$ | 98.79 | 19.20 | 66.41 | 7.74 | 100.00 |
| Sc(OTf)$_3$ | 99.58 | 25.68 | 56.64 | 8.77 | 96.43 |
| Ga(OTf)$_3$ | 99.88 | 31.59 | 49.67 | 7.39 | 92.09 |
| Sn(OTf)$_3$ | 94.06 | 12.70 | 73.49 | 8.03 | 100.00 |
| Al(OTf)$_3$ | 100.00 | 29.40 | 53.87 | 8.00 | 94.10 |
| Sulfuric | 83.63 | 6.33 | 68.34 | 6.23 | 98.87 |

COMPARATIVE EXAMPLE 9 AND EXAMPLES 13-18

The same experimental setup, procedure and conditions were used as in Comparative Example 8 and Examples 7-12 (0.1 mol percent of catalyst), except that the reaction was continued for 3 hours at 140 degrees Celsius after introduction of the catalyst, as opposed to 2 hours. The results are shown in Table 4:

TABLE 4

| Acid | % sorbitol conversion | Isosorbide yield (mol %) | 1,4-sorbitan yield (mol %) | 2,5-sorbitan yield (mol %) | Accountability (wt %) |
|---|---|---|---|---|---|
| $Bi(OTf)_3$ | 99.86 | 32.45 | 51.09 | 7.33 | 92.67 |
| $In(OTf)_3$ | 100.00 | 44.85 | 36.27 | 8.24 | 90.15 |
| $Sc(OTf)_3$ | 100.00 | 49.35 | 32.28 | 9.01 | 88.40 |
| $Ga(OTf)_3$ | 100.00 | 67.20 | 3.96 | 6.96 | 79.37 |
| $Sn(OTf)_3$ | 100.00 | 24.02 | 66.37 | 7.90 | 100.00 |
| $Al(OTf)_3$ | 100 00 | 47.13 | 31.85 | 7.70 | 88.98 |
| Sulfuric | 100.00 | 25.30 | 60.22 | 5.60 | 91.88 |

COMPARATIVE EXAMPLE 10 AND EXAMPLES 19-24

The same experimental setup and procedure were used as in previous examples, except that the reaction temperature was increased to 160 degrees Celsius, and the reaction was continued for 1 hour after introduction of the acid catalyst being evaluated (again at 0.1 mol percent). Results were as shown in Table 5:

TABLE 5

| Acid | % sorbitol conversion | Isosorbide yield (mol %) | 1,4-sorbitan yield (mol %) | 2,5-sorbitan yield (mol %) | Accountability (wt %) |
|---|---|---|---|---|---|
| $Bi(OTf)_3$ | 100.00 | 62.02 | 3.83 | 7.34 | 76.21 |
| $In(OTf)_3$ | 100.00 | 68.40 | 8.74 | 7.89 | 83.63 |
| $Sc(OTf)_3$ | 100.00 | 32.10 | 46.21 | 8.15 | 89.13 |
| $Ga(OTf)_3$ | 100.00 | 64.62 | 5.07 | 6.23 | 77.71 |
| $Sn(OTf)_3$ | 97.95 | 17.95 | 64.64 | 9.68 | 97.35 |
| $Al(OTf)_3$ | 100.00 | 48.01 | 28.48 | 7.64 | 84.05 |
| Sulfuric | 100.00 | 49.78 | 26.35 | 8.70 | 88.92 |

COMPARATIVE EXAMPLE 11 AND EXAMPLES 25-30

The acids were evaluated at a lower catalyst load of 0.05 mol percent, the lower temperature of 140 degrees Celsius and with a reaction time of two hours, with the results shown in Table 6 as follows:

TABLE 6

| Acid | % sorbitol conversion | Isosorbide yield (mol %) | 1,4-sorbitan yield (mol %) | 2,5-sorbitan yield (mol %) | Accountability (wt %) |
|---|---|---|---|---|---|
| $Bi(OTf)_3$ | 98.77 | 22.25 | 68.13 | 8.47 | 100.00 |
| $In(OTf)_3$ | 92.22 | 11.16 | 72.98 | 7.80 | 100.00 |
| $Sc(OTf)_3$ | 94.92 | 15.76 | 67.33 | 6.91 | 95.87 |
| $Ga(OTf)_3$ | 97.72 | 15.83 | 67.27 | 8.83 | 92.98 |
| $Sn(OTf)_3$ | 56.84 | 2.70 | 49.76 | 3.97 | 100.00 |
| $Al(OTf)_3$ | 80.69 | 6.37 | 69.11 | 6.34 | 100.00 |
| Sulfuric | 58.20 | 3.36 | 57.81 | 6.37 | 97.53 |

COMPARATIVE EXAMPLE 12 AND EXAMPLES 31-36

The acids were evaluated at the lower catalyst load of 0.05 mol percent used in Examples 25-30, but at the higher temperature of 160 degrees Celsius and with a reaction time of one hour rather than two after introduction of the catalyst being evaluated, with the results shown in Table 7 as follows:

TABLE 7

| Acid | % sorbitol conversion | Isosorbide yield (mol %) | 1,4-sorbitan yield (mol %) | 2,5-sorbitan yield (mol %) | Accountability (wt %) |
|---|---|---|---|---|---|
| $Bi(OTf)_3$ | 99.43 | 25.25 | 60.18 | 9.13 | 97.87 |
| $In(OTf)_3$ | 100.00 | 31.12 | 55.71 | 9.83 | 92.75 |
| $Sc(OTf)_3$ | 96.69 | 15.38 | 68.14 | 8.43 | 97.99 |
| $Ga(OTf)_3$ | 100.00 | 71.31 | 7.64 | 8.30 | 86.95 |
| $Sn(OTf)_3$ | 85.51 | 10.65 | 69.05 | 7.17 | 100.00 |
| $Al(OTf)_3$ | 100.00 | 26.08 | 58.80 | 8.85 | 95.65 |
| Sulfuric | 69.22 | 4.05 | 53.67 | 5.52 | 95.53 |

COMPARATIVE EXAMPLE 13 AND EXAMPLES 37-42

The acids were evaluated at a still lower catalyst load of 0.01 mol percent, at a temperature of 160 degrees Celsius and with a reaction time of one hour after introduction of the catalyst being evaluated, with the results shown in Table 8 as follows:

TABLE 8

| Acid | % sorbitol conversion | Isosorbide yield (mol %) | 1,4-sorbitan yield (mol %) | 2,5-sorbitan yield (mol %) | Accountability (wt %) |
|---|---|---|---|---|---|
| $Bi(OTf)_3$ | 58.18 | 2.95 | 49.02 | 4.92 | 100.00 |
| $In(OTf)_3$ | 71.67 | 5.19 | 58.41 | 6.23 | 98.70 |
| $Sc(OTf)_3$ | 40.40 | 1.74 | 34.48 | 3.43 | 99.46 |
| $Ga(OTf)_3$ | 67.72 | 4.42 | 58.30 | 6.08 | 99.65 |
| $Sn(OTf)_3$ | 71.00 | 4.86 | 58.58 | 6.10 | 99.21 |
| $Al(OTf)_3$ | 64.41 | 3.56 | 54.54 | 5.65 | 100.00 |
| Sulfuric | 26.90 | 0.00 | 26.17 | 0.61 | 99.98 |

COMPARATIVE EXAMPLE 14 AND EXAMPLES 43-44

The acids were evaluated at a still lower catalyst load of 0.005 mol percent, at a temperature of 160 degrees Celsius and with a reaction time of one hour after introduction of the catalyst being evaluated, with the results shown in Table 9 as follows:

TABLE 9

| Acid | % sorbitol conversion | Isosorbide yield (mol %) | 1,4-sorbitan yield (mol %) | 2,5-sorbitan yield (mol %) | Accountability (wt %) |
|---|---|---|---|---|---|
| $Bi(OTf)_3$ | 71.06 | 4.68 | 58.47 | 6.38 | 100.00 |
| $In(OTf)_3$ | 88.69 | 9.99 | 68.93 | 8.26 | 100.00 |
| Sulfuric | 21.10 | 0.00 | 19.22 | 0.87 | 100.00 |

COMPARATIVE EXAMPLES 15 and 16, WITH EXAMPLE 45

For these examples, two runs were conducted using differing amounts of sulfuric acid (0.1 mol percent for Comparative Example 15 and 1 mol percent for Comparative Example 16) to catalyze the dehydration of mannitol to isomannide and anhydromannitols, and the results were compared to a run using 0.1 mol percent of bismuth (III)

triflate under the same conditions of 160 degrees Celsius, one hour run time and a reduced pressure of 20 torr.

For the two sulfuric acid experiments, a three neck 250 mL round bottomed flask equipped with a magnetic stir bar was charged with 100 grams of mannitol (0.549 mol), then immersed in an oil bath maintained at 160 degrees Celsius. Once the mannitol liquefied and attained an internal temperature of 160 degrees as measured by an internal temperature probe, a condenser was outfitted onto one of the flask necks and vacuum was initiated. The sulfuric acid was then introduced via syringe through a rubber septum capped neck. After an hour, the vacuum was broken, and the crude product mixture was cooled, weighed and quantitatively analyzed by gas chromatography.

For the run with the inventive bismuth triflate catalyst, a three neck 250 ml round bottomed flask was charged with the mannitol and with 360 milligrams of the bismuth triflate catalyst, than immersed in the 160 degree Celsius oil bath. Once the mannitol liquefied and the bismuth triflate dissolved in the mannitol, and as the mixture achieved an internal temperature of 160 degrees Celsius, then a condenser was outfitted onto one of the flask necks and vacuum was initiated down to a pressure of 20 torr. After one hour, the vacuum was broken, and the crude product mixture was cooled, weighed and quantitatively analyzed by gas chromatography.

The results were that 100% conversion of the mannitol was realized in all three runs, the yields of isomannide (expressed in mol percents) were much greater using the bismuth triflate catalyst: sulfuric acid at 0.1 mol percent gave only 2 percent of isomannide, whereas at 1 mol percent addition the isomannide yield was 25 percent. However, by comparison, the inventive bismuth triflate gave 61 percent of isomannide.

What is claimed is:

1. A process for producing an isohexide from a starting material of one or both of a hexitol and a monoanhydrohexitol, comprising contacting the starting material with from 0.005 mol percent to 0.1 mol percent of a homogeneous Lewis acid catalyst selected from the group consisting of bismuth (III) triflate, gallium (III) triflate, scandium (III) triflate, aluminum triflate, indium (III) triflate, tin (II) triflate and combinations of two or more of these, at a temperature of from 140 degrees to 160 degrees and over a period of from 1 hour to 3 hours, under reduced pressure and with continuous removal of water from the product mixture in the course of the dehydration.

2. The process of claim 1, wherein the starting material is sorbitol.

3. The process of claim 1, wherein the starting material is mannitol and the catalyst is bismuth (III) triflate.

* * * * *